(12) United States Patent
Singal et al.

(10) Patent No.: US 11,191,864 B1
(45) Date of Patent: Dec. 7, 2021

(54) DEVICE TO PROVIDE PERSONAL, PORTABLE, AND CONTINUOUS SUPPLY OF STERILIZED/PURIFIED BREATHABLE AIR AND TO DISINFECT EXHALED AIR

(71) Applicants: Krishan Kumar Singal, Severna Park, MD (US); Gaurav Singal, Newton, MA (US)

(72) Inventors: Krishan Kumar Singal, Severna Park, MD (US); Gaurav Singal, Newton, MA (US)

( * ) Notice: Subject to any disclaimer, the term of this patent is extended or adjusted under 35 U.S.C. 154(b) by 0 days.

(21) Appl. No.: 17/204,838

(22) Filed: Mar. 17, 2021

Related U.S. Application Data

(60) Provisional application No. 63/034,351, filed on Jun. 3, 2020.

(51) Int. Cl.
*A61L 9/20* (2006.01)
*A61M 16/06* (2006.01)

(52) U.S. Cl.
CPC ............ *A61L 9/20* (2013.01); *A61M 16/0683* (2013.01); *A61L 2209/15* (2013.01); *A61M 2205/053* (2013.01)

(58) Field of Classification Search
CPC ........ A41D 13/1146; A61B 2018/2261; A61B 18/00; A61B 18/08; A61B 18/084; A61B 23/025; A61B 23/06; A61L 2/0011; A61L 2/10; A61L 2209/111; A61L 2209/12; A61L 2209/134; A61L 2209/14; A61L 2209/15; A61L 9/20; A61L 9/22; A61M 1/3681; A61M 1/3683; A61M 15/0088; A61M 15/009; A61M 16/0078; A61M 16/06; A61M 16/0683; A61M 16/0816;
(Continued)

(56) References Cited

U.S. PATENT DOCUMENTS 2,671,445 A * 3/1954 Charbonnel ........... A62B 18/00
128/201.12
3,139,885 A * 7/1964 Hirtz ................. A61M 15/0016
128/203.27
(Continued)

FOREIGN PATENT DOCUMENTS

AU 2020100503 A4 5/2020
CN 111053984 A 4/2020
(Continued)

Primary Examiner — Annette Dixon
(74) Attorney, Agent, or Firm — Rahman LLC

(57) ABSTRACT

A device to provide sterilized and purified breathable air and to disinfect exhaled air and includes a housing having a first and second opening. The housing includes at least one partition having a plurality of holes, and within the housing such that a plurality of compartments is formed between the first opening and the second opening, and at least one ultraviolet (UV) light source positioned in each of the plurality of compartments. The UV light source is UVC LED lights to emit UVC light of a predefined wavelength within the plurality of compartments to sterilize and purify the air while flowing through the housing. The device includes a mask fluidically coupled to the second opening of the housing using a flexible second pipe to provide the purified air. The device includes one-way valves at the second opening of the housing, and two one-way valves at the outlets of the mask.

15 Claims, 5 Drawing Sheets

(58) Field of Classification Search
CPC .......... A61M 16/0833; A61M 16/1065; A61M 2202/0208; A61M 2205/3606; A61M 2205/366; A61M 2206/14; A61N 5/0601; B01D 2275/10; B01D 45/04; B01D 46/0032; B01D 46/10; B01D 46/2411; B01D 46/44; Y10S 55/35
See application file for complete search history.

(56) References Cited

U.S. PATENT DOCUMENTS

| | | | |
|---|---|---|---|
| 5,165,395 A * | 11/1992 | Ricci | A41D 13/1146 128/202.22 |
| 5,637,877 A * | 6/1997 | Sinofsky | A61L 2/10 250/492.1 |
| 5,701,886 A * | 12/1997 | Ryatt | A61M 16/06 128/200.14 |
| 6,464,936 B1 * | 10/2002 | Mowat | A61L 2/0011 422/22 |
| 6,595,207 B1 | 7/2003 | McDonald et al. | |
| 6,691,706 B2 | 2/2004 | Ives | |
| 7,523,750 B2 | 4/2009 | Krzysztofik | |
| 7,658,891 B1 | 2/2010 | Barnes | |
| 8,733,356 B1 * | 5/2014 | Roth | A61L 9/20 128/205.27 |
| 8,960,190 B2 | 2/2015 | James et al. | |
| 10,029,797 B2 | 7/2018 | Space et al. | |
| 2008/0232092 A1 | 9/2008 | Carter | |
| 2009/0004047 A1 | 1/2009 | Hunter et al. | |
| 2009/0205664 A1 | 8/2009 | Lyon | |
| 2012/0199003 A1 | 8/2012 | Melikov et al. | |
| 2012/0279503 A1 * | 11/2012 | Zhou | A41D 13/1192 128/205.27 |
| 2014/0363333 A1 | 12/2014 | Carr | |
| 2016/0121145 A1 | 5/2016 | Hopermann et al. | |
| 2018/0001049 A1 * | 1/2018 | Schuller | B01D 53/0415 |
| 2018/0064968 A1 * | 3/2018 | Taslagyan | A61L 9/20 |
| 2018/0214585 A1 | 8/2018 | Piper | |
| 2021/0077762 A1 * | 3/2021 | Mauger | A61M 16/06 |

FOREIGN PATENT DOCUMENTS

| | | |
|---|---|---|
| DE | 202020101798 U1 | 4/2020 |
| JP | 2007202826 A | 8/2007 |
| KR | 10-2019-0138151 A | 12/2019 |
| KR | 10-2020-0020747 A | 2/2020 |
| NO | 20200374 A1 | 4/2020 |

\* cited by examiner

DEVICE TO PROVIDE PERSONAL, PORTABLE, AND CONTINUOUS SUPPLY OF STERILIZED/PURIFIED BREATHABLE AIR AND TO DISINFECT EXHALED AIR

CROSS-REFERENCE TO RELATED APPLICATION

This application claims priority to U.S. Provisional Patent Application No. 63/034,351 filed on Jun. 3, 2020, the complete disclosure of which, in its entirety, is herein incorporated by reference.

BACKGROUND

Technical Field

The embodiments herein generally relate to air purifiers and breathable masks. More particularly, the embodiments herein relate to a compact, efficient, and easily operable device to provide a personal, portable, and continuous supply of sterilized/purified breathable air and to disinfect exhaled air.

Description of the Related Art

This background description includes information that may be useful in understanding the general scope of the present disclosure. It is not an admission that any of the information provided herein is prior art or relevant to the presently claimed invention, or that any publication specifically or implicitly referenced is prior art.

An infection is caused by the invasion of the body by an organism such as a bacteria, virus, or parasite, etc. Such pathogens may be transmitted by several routes such as an insect bite (e.g., malaria), animal bite (e.g., rabies), contact with other people (e.g., leprosy), contact with bodily fluids (e.g., HIV), eating contaminated food (e.g., typhoid), drinking impure water (e.g., giardiasis), and breathing contaminated air (e.g., common cold, influenza), among others.

The prevention of infection generally begins by avoiding contact with the infectious agent. Most people can understand how best to try to avoid being bitten by mosquitos, going near rabid animals, drinking unpurified water, etc. However, avoiding breathing contaminated air becomes challenging if one wishes to live a normal life and interact with society. Humans generally cannot hold their breath longer than a few minutes at a time. Moreover, humans typically breathe about 300 liters of air every hour. Accordingly, it is difficult to routinely carry bottled air for several hours (as opposed to food in a bag or water in a bottle, for example). Further, absent specialized equipment, humans typically cannot easily determine when the surrounding air is contaminated with these pathogens. Indeed, the difficulty of preventing airborne virus infections is highlighted by the coronavirus 2 (SARS-CoV-2) pandemic.

Attempts are being made to purify the air in contained environments such as by using air purifiers, disinfectants, and filtration, etc. However, such techniques tend to limit the mobility of people. Moreover, to avoid breathing contaminated air, people attempt to use masks to help filter out viruses with limited success. Sunlight can prevent the growth of micro-organisms. Moreover, the most effective bactericidal wavelengths are between 250 to 280 nanometers. The mechanism of injury to the microorganism is through the effect of UV-C on DNA/RNA rather than proteins. When an infected person coughs or sneezes, droplets containing infectious organisms are projected into the air as aerosols. These droplets quickly dry by evaporation and leave behind nuclei that can remain suspended in the air for a long time. Inhalation of such contaminated air can result in an infection to humans and animals. Tuberculosis is easily spread by a droplet of infectious organisms and exposing the contaminated air to ultraviolet light can prevent the spread of infection.

Ultraviolet light may be used for Upper Room Air disinfection, water disinfection, and for air disinfection in HVAC systems. Ultraviolet may be used for destroying germs and may be produced by low-pressure mercury lamps. However, these devices tend to be cumbersome, use a lot of power, and produce ozone as a byproduct. Ultraviolet light is classified as UV-A, UV-B, and UV-C depending on the wavelength with UV-C being the shortest of the three. Though present in sunlight, UV-C is almost completely blocked in the Earth's upper atmosphere. Only UV-A and UV-B reach the Earth's surface in significant quantities. UV-C has very little depth of penetration and is absorbed by the outer dead layer of skin in humans. However, erythema and photokeratitis can occur upon overexposure to UV-C.

Some conventional solutions, such as those described in the cited references below, have been utilized to supply air and/or to provide air purification. The complete disclosures of all these references are incorporated by reference herein for the purposes of providing the scope of the conventional solutions, and not for limitation purposes. However, while these solutions may have been suitable for their specific applications, they contain some shortcomings that have not been overcome in the industry.

U.S. Patent Application Publication No. 2009/0004047 published to Hunter et al. on Jan. 1, 2009 utilizes a fan to blow air in a sterilization chamber and utilizes the blower pressure magnification with UV lenses to supply the air. However, fans tend to have large power requirements, thus making the apparatus unsuitable for convenient portability purposes and applications. U.S. Patent Application Publication No. 2009/0205664 published to Lyon on Aug. 20, 2009 utilizes a sterilization system containing UVC bulbs, ozone gas, and a fan to circulate the air. Ozone gas must be removed by the system prior to inhalation by a user due to its toxicity. This, in conjunction with the use of fans, requires a significant amount of power to ensure proper functioning of the system, which reduces the efficiency of the system and reduces the ease of portability. U.S. Pat. No. 7,658,891 issued to Barnes on Feb. 9, 2010 utilizes mercury vapor with UVC light and ozone gas to sterilize a hazmat suit, helmet, and mask. However, this apparatus is not used for providing inhaled sterilized air, but rather is used to sterilize equipment. Furthermore, the use of ozone gas in this apparatus means that it generally cannot be used for providing inhaled air due to the toxicity of ozone. Moreover, this apparatus is large and bulky utilizing a fan, which necessitates high power requirements and reduces the ease of portability for users. U.S. Patent Application Publication No. 2016/0121145 published to Hopermann et al. on May 5, 2016 provides a maintenance device to maintain a breathing apparatus. This device is often used with conventional breathing systems to remove toxic chemicals such as ozone that may build up in the system, but is not generally used as a portable device for users.

Accordingly, there is, therefore, a need for a new highly portable technique for providing purified air for breathing purposes, which does not rely on high power consumption peripheral components such as fans, or the use of toxic ozone gas, or requires the need for specialized maintenance equipment to decontaminate the system after use.

SUMMARY

In view of the foregoing, the embodiments herein provide a portable device carried by a user such that the device provides a continuous supply of sterilized air to allow the user to move about freely while breathing purified air, even in contaminated ambient surroundings.

The embodiments herein provide a portable device ("device") to provide a personal, portable, and continuous supply of sterilized/purified breathable air and to disinfect exhaled air. The portable device may comprise a housing having a first opening and a second opening. The housing may comprise partition(s) having a plurality of holes, being configured within the housing such that a plurality of compartments are formed between the first opening and the second opening of the housing. The housing may comprise an elongated semi-circular flexible first tube adapted to be worn by the user. The inside portion of the housing and both surfaces of the partition are covered/painted with UVC (also referred to as UV-C, herein) reflective material. Further, UVC producing LEDs are provided in each of the compartments of the housing. A first one-way valve is provided in the housing to allow outflow of air from the second opening and restrict the inflow of air into the housing through the second opening. Breathable air is discharged through the first one-way valve into a flexible second tube that connects to a breathing mask. The breathing mask contains two additional one-way valves to permit exhaled air to be discharged from the breathing mask. The portable device may assist in allowing a user to breathe purified air when the ambient air proves to be dangerous; e.g., when the ambient air is contaminated with unhealthy pollutants and/or infectious agents such as in mass transit vehicles (e.g., buses, trains, airplanes, etc.) at the time of epidemics/pandemics, and to protect people in the event of bio-terrorism or soldiers and first responders in biological warfare scenarios.

In certain embodiments, the housing may be in form of a flexible first tube having the first opening and the second opening at two opposite ends of the flexible first tube, and the partition(s) may be a perforated disc having multiple holes. The flexible first tube may be divided into three sections or compartments by the partitions. The inside portion of the flexible first tube and both surfaces of the partitions may be covered/painted with UVC reflective material. Further, UVC producing LEDs may be provided in each of the three sections of the flexible first tube. A first one-way valve is provided in the flexible first tube. Breathable air is discharged from the flexible first tube through the first one-way valve into the flexible second tube that connects to the breathing mask.

According to another aspect, the embodiments herein provide a housing that acts as a sterilizing chamber to provide a personal, portable, and continuous supply of sterilized/purified air. The housing defines the body of the device and has a first opening and a second opening. The housing comprising partition(s) having a plurality of holes, being configured within the housing such that a plurality of compartments is formed between the first opening and the second opening of the housing. The inside portion of the housing and both surfaces of the partition are covered/painted with UVC reflective material. Further, UVC producing LEDs are provided in each of the compartments of the housing. A first one-way valve is provided in the housing to allow outflow of air from the second opening and restrict the inflow of air into the housing through the second opening.

The device can be configured to be of any suitable size, shape, and configuration and can be constructed using any suitable material, the number and power capacity of components such as LEDs, and power source(s), etc. may also be suitably selected. Furthermore, the breathing mask can be individualized for better user fit. Since the LEDs provide the pathogen destroying UVC and the system does not produce ozone gas, there is no need for specialized equipment for the removal of the ozone gas or specialized maintenance equipment. Accordingly, the device is always ready for portable use without undergoing maintenance for decontamination or requiring heavy peripheral equipment for proper functioning.

Another embodiment provides a portable device to provide sterilized and purified breathable air and to disinfect exhaled air for a user, the device comprising a breathing mask; a housing operatively connected to the breathing mask, wherein the housing comprises a first opening and a second opening, wherein the housing comprising at least one partition having a plurality of holes, being configured within the housing such that a plurality of compartments is formed between the first opening and the second opening, and wherein the housing comprises an elongated semi-circular flexible first tube adapted to be worn by the user; and at least one ultraviolet (UV) light source positioned in each of the plurality of compartments, the at least one UV light source configured to emit UV light of a predefined wavelength within the plurality of compartments, wherein when air is expelled through the second opening, air inflows into the housing without a fan or pump from the first opening and flows towards the second opening through each of the plurality of compartments such that the air flowing through the housing gets sterilized and purified by the emitted UV light, and the sterilized and purified air flows out from the second opening.

The breathing mask may be adapted to be worn over any of a mouth and nose of a user, and the second opening of the housing is fluidically coupled to the breathing mask by a flexible second tube and configured to supply the sterilized and purified air to the user. The breathing mask may comprise an inlet fluidically coupled to the second opening of the housing, and at least one outlet to facilitate outflow of air being exhaled by the user. When air is exhaled by the user into the housing, using the breathing mask, through the second opening, the exhaled air flows from the second opening towards the first opening through each of the plurality of compartments such that the exhaled air flowing through the housing gets sterilized and purified by the emitted UV light, and the sterilized and purified air flows out from the first opening into atmosphere. The housing may comprise a first one-way valve being configured at the second opening to allow outflow of air from the second opening, and restrict inflow of air into the housing through the second opening. The breathing mask may comprise a second one-way valve being configured at each of the at least one outlet to allow outflow of the exhaled air, and restrict inflow of air into the breathing mask through the at least one outlet.

Any or a combination of an inner surface of the housing, and surface of the at least one partition may be coated with a UVC reflective material. The flexible first tube may be adapted to be accommodated over any or a combination of a shoulder, neck, waist, and arms of the user. The housing may comprise aluminum, and an outer surface of the housing may be covered with a cellophane wrap. One of the at least one partition may be configured at the first opening, and other at least one partition may be configured at predefined positions along a length of the housing between the first opening and the second opening. The at least one UV light source may be a UVC LED light.

The device may comprise an electrical power unit electrically coupled to the at least one UV light source, and configured to supply electrical power to the at least one UV light source. The electrical power unit may comprise any or a combination of a charging adapter, batteries, power bank, USB charging port, and electrical power source. A peripheral shape of the at least one partition may be based on a profile of an internal surface of the housing such that there is no gap between the at least one partition and the corresponding inner surface of the housing, and the at least one partition allows air to flow only through the corresponding plurality of holes. The housing may be configured as a flexible first tube having the first opening and the second opening at two opposite ends of the flexible first tube, and the at least one partition may be configured as a disc. A diameter of the partition may be equal to an internal diameter of the flexible first tube such that there is no gap between the inner surface of the flexible first tube and the corresponding partition, and the partition allows air to flow only through the plurality of holes of the corresponding partition.

Another embodiment provides a device to facilitate sterilization and purification of air, the device comprising a housing defining a chamber and having a first opening and a second opening, the housing comprising at least one partition having a plurality of holes, being configured within the housing such that a plurality of compartments are formed between the first opening and the second opening, and wherein the housing is configured as an elongated semicircular flexible first tube adapted to be worn by a user; and at least one UV light source positioned in each of the plurality of compartments, the at least one UV light source configured to emit UV light of a predefined wavelength within the plurality of compartments, wherein when air is expelled through the second opening, air inflows into the housing without a fan or pump from the first opening and flows towards the second opening through each of the plurality of compartments such that the air flowing through the housing gets sterilized and purified by the emitted UV light, and the sterilized and purified air flows out from the second opening.

The housing may be a flexible first tube having the first opening and the second opening at two opposite ends of the flexible first tube, and the at least one partition may be configured as a disc, and wherein the at least one UV light source may be a UVC LED light. The second opening of the housing may be adapted to be fluidically coupled to any or a combination of a breathing mask, and directly to a mouth and nose of a user, using a flexible second tube. The second opening of the housing may be fluidically coupled to a breathable storage tank using any or a combination of a mechanical pump, automated pump, and a pipe, which are configured to supply and store the sterilized and purified air from the housing into the storage tank.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1:
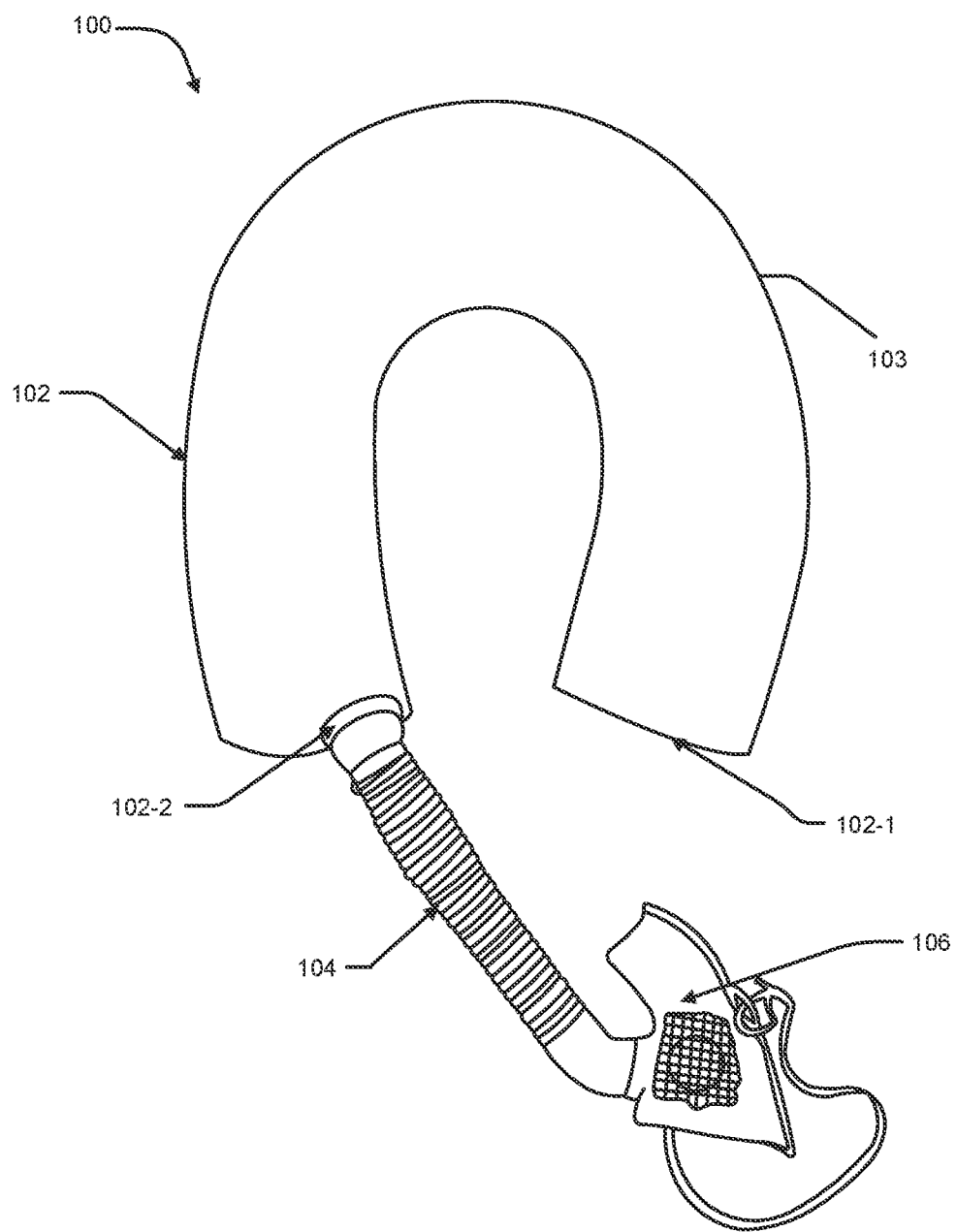
FIG. 1 illustrates an exemplary view of a sterilization device according to an embodiment herein.

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Various terms are used herein. To the extent a term used in a claim is not defined below, it should be given the broadest definition persons in the pertinent art have given that term as reflected in printed publications and issued patents at the time of filing.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all groups used in the appended claims.

In the specification, reference may be made to the spatial relationships between various components and to the spatial orientation of various aspects of components as the devices are depicted in the attached drawings. However, as will be recognized by those skilled in the art after a complete reading of the present application, the devices, members, components, etc. described herein may be positioned in any desired orientation. Thus, the use of terms such as "above," "below," "upper," "lower," "first", "second" or other like terms to describe a spatial relationship between various components or to describe the spatial orientation of aspects of such components should be understood to describe a relative relationship between the components or a spatial orientation of aspects of such components, respectively, as the device described herein may be oriented in any desired direction. Referring now to the drawings, and more particularly to FIGS. 1 through 5, where similar reference characters denote corresponding features consistently throughout the figures, there are shown examples of the embodiments herein. In the drawings, the size and relative sizes of components, layers, and regions, etc. may be exaggerated for clarity.

As illustrated in FIGS. 1 through 5, according to an embodiment herein, a device 100 provides sterilized and purified breathable air and to disinfect exhaled air. The device 100 (also referred to as portable device 100 herein) can include a housing 102 having a first opening 102-1 and a second opening 102-2. The housing 102 can include at least one partition 202-1 to 202-4 having a plurality of holes (also referred to as holes, hereinafter), being configured within the housing 102 such that a plurality of compartments 204-1 to 204-3 is formed between the first opening 102-1 and the second opening 102-2. In an embodiment, the at least one partition 202-1 to 202-4 can be a flat member having a peripheral shape based on a profile of an internal surface of the housing 102 such that there is no gap between the at least one partition 202-1 to 202-4 and the corresponding inner surface of the housing 102, and the housing 102 allows air to flow only through the holes of the corresponding partitions 202. In another embodiment, housing 102 can be in the form of a flexible first tube 103 having the first opening 102-1 and the second opening 102-2 at two opposite ends. Further, the at least one partition 202-1 to 202-3 can be configured as a perforated disc with the holes. The at least one partition 202-1 to 202-3 can have a diameter equal to an internal diameter of the housing 102 such that there is no gap between the at least one partition 202-1 to 202-3 and the corresponding inner surface of the flexible first tube 103, and the flexible first tube 103 allows air to flow only through the holes of the corresponding at least one partition 202-1 to 202-3. Partition 202-4 may be a suitably shaped disc structure positioned at the end of the housing 102 that provides for a directed flow of the air out of the housing 102.

The device 100 can include at least one UV light source 206-1 to 206-3 positioned in each of the plurality of compartments 204-1 to 204-3, such that the at least one UV light source 206-1 to 206-3 are configured to emit UV light of a predefined wavelength within the plurality of compartments 204-1 to 204-3. The at least one UV light source 206-1 to 206-3 can be a UVC LED light, which is capable of producing ultraviolet light at the predefined wavelengths, and high efficiency, with a very small amount of power at low voltage levels for a longer period of time. In addition, because the at leave one UV light source 206-1 to 206-3 may be configured as a LEDs, they produce no ozone and very little heat.

Figure 4:
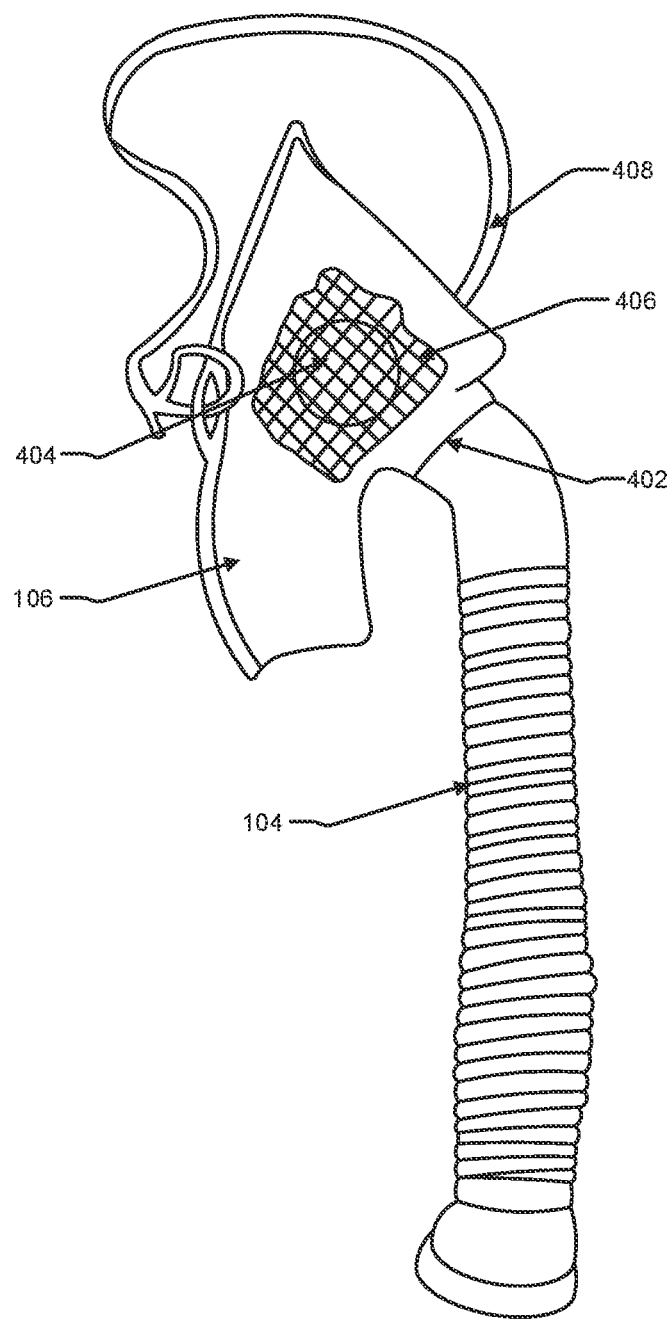
FIG. 4 illustrates an exemplary view of a breathing mask being connected to a flexible second tube of the device of FIG. 1, according to an embodiment herein.
Figure 5:
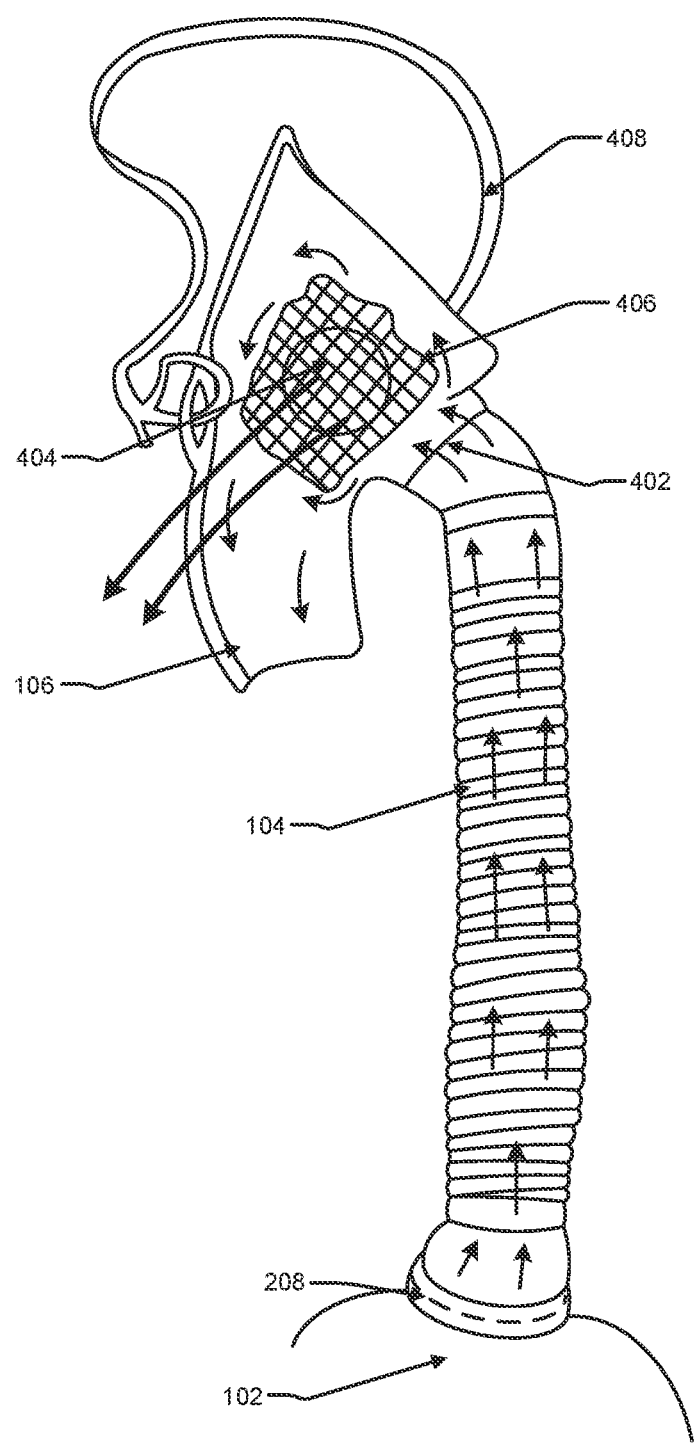
FIG. 5 illustrates the flow of air from the housing to the breathing mask through the flexible second tube in the device of FIG. 1, according to an embodiment herein.

The device 100 can include a breathing mask 106 adapted to be worn over any or a combination of the mouth and nose of a user (not shown). The second opening 102-2 of the housing 102 can be fluidically coupled to the breathing mask 106 by a flexible second tube 104 and the housing 102 can be configured to supply the sterilized and purified air to the user. Referring to FIGS. 4 and 5, the breathing mask 106 can include an inlet 402 fluidically coupled to the second opening 102-1 of the housing 102 through the flexible second tube 104, and at least one outlet 404 (also referred to as outlet(s) 404, herein) to facilitate outflow of air being exhaled by the user. The breathing mask 106 can further include a strap 408 to facilitate the user to accommodate the breathing mask 106 over his/her face.

In an embodiment, the housing 102 can include a first one-way valve 208 can be configured at the second opening to allow outflow of air from the second opening 102-2, and restrict the inflow of air into the housing 102 through the second opening 102. In addition, the breathing mask 106 can also include a second one-way valve 406 being configured at each of the outlet(s) 404 to allow outflow of the exhaled air, but restrict the inflow of air into the breathing mask 106 through the outlet(s) 404. In another embodiment, the second opening 102-2 can be adapted to be directly fluidically coupled to any or a combination of mouth and nose of a user, using a flexible second tube 104, so that the sterilized and purified can be provided to the user without the use of any breathing mask. In another embodiment, an inner surface of the housing 102, and surfaces of the at least one partition 202-1 to 202-4 can be coated with a UVC reflective material, to increase the intensity of ambient radiation within the housing 102 with the radiation of the UVC light.

Figure 2:
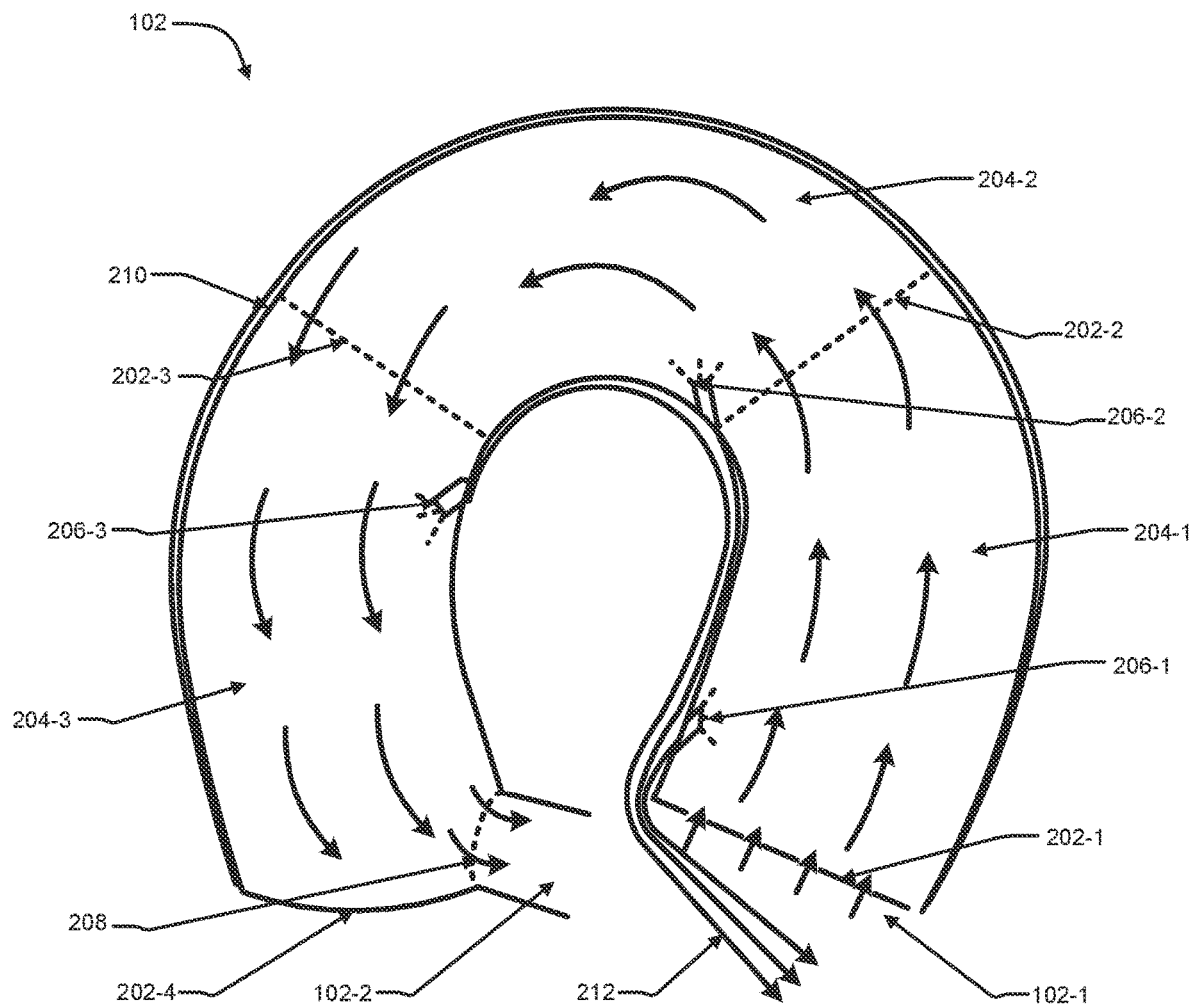
FIG. 2 illustrates an exemplary cross-sectional view of a housing of the device of FIG. 1, according to an embodiment herein.

Referring to FIGS. 2 and 5, in an implementation, when the user inhales air using the breathing mask 106, the air is expelled from the housing 102 through the second opening 102-1, which causes ambient air that may contain pathogens to inflow into the housing 102 from the first opening 102-1 and flow towards the second opening 102-2 through each of the plurality of compartments 204-1 to 204-3 such that the ambient air flowing through the housing 102 traverses through the partitions 202-1 to 202-3, get sterilized and purified by the emitted UVC light from the UV light source 206-1 to 206-3, and the sterilized and purified air finally flows out from the first one-way valve 208 at the second opening 102-2 of the housing 102 to the breathing mask 106 of the user. Further, when the user exhales air, the first one-way valve 208 of the housing 102 can restrict the exhaled to enter into the housing 102 through the second opening 102-2, and the exhaled air can flow out of the breathing mask 106 only through the second one-way valve 406 present at the outlet(s) 404 of the breathing mask 106.

In another implementation (not shown), when air is exhaled by the user into the breathing mask 106, the exhaled air can enter into the housing 102 through the flexible second tube 104 and the second opening 102-2, and can flow from the second opening 102-2 towards the first opening 102-1 through each of the plurality of compartments 204-1 to 204-3 such that the exhaled air flowing through the housing 102 gets sterilized and purified by the emitted UVC light from UV light source 206-1 to 206-3, and finally the sterilized and purified exhaled air flows out from the first opening 102-1 into the ambient atmosphere.

It is challenging to define and isolate the volume of air that requires disinfection rather than the entire atmosphere.

Using a housing 102 with a volume of about 1.5 to 2 liters, the air can be disinfected prior to being breathed in and/or after being exhaled. As the air in the housing 102 is breathed in, it is replaced with air from the atmosphere. The exhaled air is disinfected prior to being released into the atmosphere thus decreasing the chance of infecting people and animals and contaminating objects nearby.

By breathing air through the breathing mask 106 that allows the flow of air in one direction only, the source and location of the breathable air can be controlled. An average person takes about 12 breaths a minute and inhales about 500 milli liters (mls) per breath. The housing 102 of 1,500 mls volume would have sufficient air for three breaths. By allowing the air to flow in one direction through the housing 102, one could treat the air for about 15 seconds before being inhaled by the user. By installing the LEDs (UV light source 206-1 to 206-3) producing UVC in the housing 102, this provides up to 15 seconds to sterilize the air in the housing 102.

Similarly, by breathing out (or exhaling air) into the breathing mask 106 with the first one-way valve 208, the exhaled air can be passed through the housing 102. Again, the exhaled air can get treated for about 15 seconds before being released into the atmosphere, thus reducing ambient contamination.

The extent of inactivation of pathogens is directly proportional to the duration of exposure and to the intensity of the radiation. The intensity of ambient radiation being produced by the UVC LEDs (i.e., at least one UV light source 206-1 to 206-3) within the housing 102 can be increased by UVC reflective material being coated within the housing 102. Further, by having the air move sequentially from one compartment 204-1 to 204-3 to another within housing 102, it is ensured that every 500 mls of the air gets exposed to UVC for approximately 15 seconds.

In an embodiment, the housing 102 can be in the form of a flexible first tube 103, which can be adapted to be accommodated over any or a combination of shoulder, neck, waist, and arms, but not limited to the likes, of the user so that the user can easily carry the device 100 and the housing 102 along with him/her in a portable manner.

In an embodiment, the device 100 can include an electrical power unit 300 being electrically coupled to the UV light sources 206-1 to 206-3. The electrical power unit 300 can include any or a combination of a charging adapter, batteries, power bank, mobile phone, USB charging port, and electrical power source, but not limited to the likes, which are configured to supply electrical power to the UVC LED lights (i.e., at least one UV light source 206-1 to 206-3).

Figure 3:
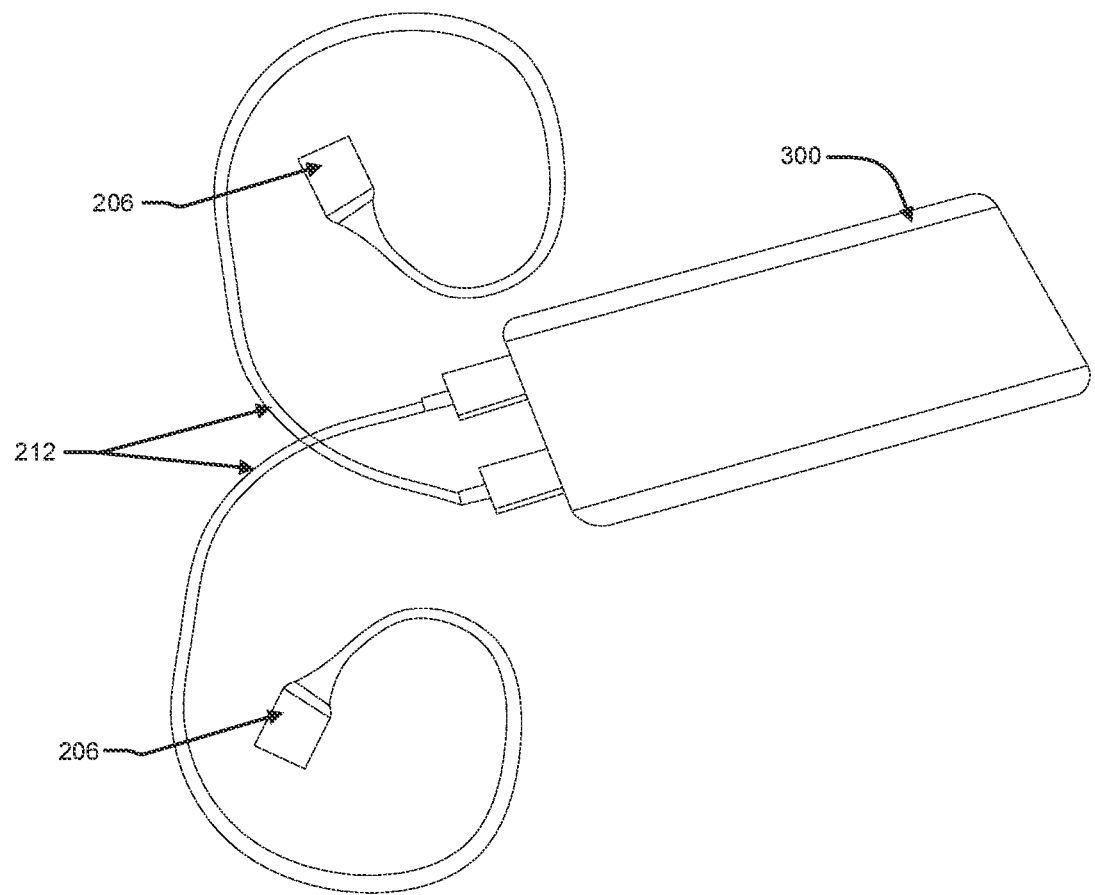
FIG. 3 illustrates an exemplary view of a mobile device powering UVC LED lights of the device of FIG. 1, according to an embodiment herein.

The device 100 provided by the embodiments herein is configured so that the housing 102 can be configured to be worn on the shoulders of a user and is in the shape of a neck pillow (although other shapes and configurations are possible), and such that the front compartment (e.g., compartment 204-3) either feeds air into the breathing mask 106 via a first one-way valve 208 or receives exhaled air from the breathing mask 106. The direction of airflow (to or from the housing 102) is controlled by the second one-way valve(s) 406 on the breathing mask 106. Referring to FIG. 3, LED lights 206 (e.g., UV light sources 206-1 to 206-3) can be powered by electrical power unit 300 such as mobile devices including a portable power pack or mobile phone, and the likes, making the device fully self-contained. The duration of the supply of purified air can be increased by recharging the electrical power unit 300 with a standard USB device.

The device 100 provided by the embodiments herein can be manufactured in the following example method. The specific parameters, values, amounts, ranges, materials, types, brands, etc. described herein are approximates and are merely selected for as examples, and as such the embodiments herein are not limited to the specific descriptions below.

The first one-way valve 208 can be similar to valves as used for CPR delivery mechanisms, and is placed at one end of the housing 102 such that the air can only exit from the second opening 102-2 of the housing 102 but not enter therethrough. The first one-way valve 208 can later be attached to the flexible second tube 104 for the breathing mask 106, as further described below.

In an exemplary embodiment, four, 3-inch diameter plastic partitions 202-1 to 202-4 can be prepared for placement in the housing 102. Two of the partitions 202-2 and 202-3 can be for internal partitioning of the housing 102, and two of the partitions 202-1 and 201-4 can be provided as end pieces of the housing 102. The end pieces (e.g., partitions 202-1 and 201-4) can be painted with UVC reflective paint on the inside surfaces only. Further, the end piece (partition 202-1) near the first opening 102-1 can be provided with holes to allow the flow of air therethrough. Holes can be drilled into the endpiece on the side opposite to the flexible second tube 104 to allow for air intake. The partition 202-4 on the side of the one-way valve 208 can be left impervious. The partitions 202-1 and 202-4 at the ends can be attached to the housing 102 and sutured in place. The other two partitions 202-2 and 202-3 (e.g., for internal partitioning) can be drilled with holes and painted on both sides with UVC reflective paint. These partitions 202-2 and 202-3 can then be sutured in place, one each at the location of the two cuts previously made in the housing 102. Then, the two cuts themselves are sewn closed. Duct tape, or other suitable sealing mechanisms, may be used to make connections airtight. The result is three connected chambers (i.e., plurality of compartments 204-1 to 204-3) of 3-inch diameter and about 8-inch length (volume over 900 mls each) as shown in FIG. 2.

Three UVC producing LED lights 206-1 to 206-3, that operate using milliamps of current at 5 volts power input, and meant for sterilization of air can be used in the housing 102. These lights 206-1 to 206-3 (collectively LEDs 206) can be wired to a cable 212 with USB A type male connectors, for example. These USB A connectors can be plugged into an electrical power unit 300 such as commercially available "power banks (e.g., such as those used to charge mobile phones), or directly to mobile phones, as shown in FIG. 3. The UVC LED lights 206-1 to 206-3 can produce the predefined wavelength of light, and can be selected and/or controlled depending upon the specific sensitivity of particular pathogens present in the air.

In an exemplary embodiment, the housing 102 can be made of aluminum, but not is not limited to aluminum. Further, side holes can be created in the housing 102, one each in the plurality of compartments 204-1 to 204-3 of the housing 102. The UVC producing LED lights 206-1 to 206-3 can then be inserted into the housing 102 (e.g., one in each compartment 204-1 to 204-3) and sutured in place. The power cables 212 of the LED lights 206-1 to 206-3 can be tacked along the outside of the housing 102. The side holes can be sealed using duct tape. The entire aluminum housing 102 can then be wrapped in a plastic cellophane wrap to make it airtight. The entire device 100 can then be placed in a specially prepared soft cloth 210 covering as shown in FIG. 2 to give the housing 102, the shape, and feel of a neck pillow.

A plastic facemask, such as one used for nebulizer treatments, can be provided as the breathing mask 106. Two outlets 404 or side holes of the breathing mask 106 can be reinforced with netting and a piece of plastic cellophane wrap attached to the outside. This results in two one-way valves 406 that allow the air to leave the breathing mask 106 but not enter it. Further, a flexible second tube 104 can be used to connect the breathing mask 106 with the one-way valve 208 of the housing 102 as shown in FIG. 5.

Since the device 100 disallows inhalation of untreated air, the user can go into an area containing a contaminated atmosphere knowing that all the air being inhaled has indeed been sterilized. The device 100 can be sectioned into a plurality of compartments 204-1 to 204-3. Each compartment 204-1 to 204-3 of the device 100 holds more than enough air needed for an average breath; for an average of approximately five seconds. In each compartment 204-1 to 204-3, there is a source of UV-C light 206-1 to 206-3 and the interior walls of each compartment 204-1 to 204-3 are highly reflective of UV-C. The reflections back and forth eliminate "dark areas" and create a high intensity of UV-C throughout the plurality of compartments 204-1 to 204-3, thereby ensuring uniform and sustained exposure of the air to the disinfecting UVC. After approximately five seconds, for example, of sustained irradiation in the first compartment 204-1, the air goes to the second compartment 204-2 where the air is treated similarly before proceeding to the third compartment 204-3 for similar treatment. After being exposed to sterilizing UV-C for approximately five seconds, for example, once again, this thrice sterilized air volume is ready to be inhaled by the user. The exposure intensity and duration of the UV-C light are quantifiable and adjustable by controlling the power input into the UV light sources 206-1 to 206-3 and/or by increasing/decreasing the number of LEDs used for the UV light sources 206-1 to 206-3. Furthermore, the plurality of compartments 204-1 to 204-3 are each self-contained, and offer redundancy in the event of an LED failure in any particular compartment 204-1 to 204-3 or location inside the housing 102.

Further, because the primary mode of sterilization in the device 100 is UV-C, extraneous filters with resultant high resistance to airflow are avoided. Therefore, a user can breathe without requiring pressure support from a fan/blower, thereby avoiding the need for a large power supply or heavy/bulky peripheral equipment. In comparison with a blower, LEDs use a minuscule amount of power. As such, the reduced requirement for power makes the device 100 and housing 102 provided by the embodiments herein conveniently portable.

Conventional mercury UV lamps produce ozone, which is toxic to the lungs. They generate UV radiation in all wavelengths—A, B, and C. Of these, only UV-C has the ability to sterilize. UV-A and UV-B have essentially wasted outputs along with heat. The LEDs used for the UV light sources 206-1 to 206-3 and utilized in accordance with the embodiments herein avoid all of these shortcomings; i.e., no ozone, very little heat, and specifically germicidal radiation at low power consumption, among other attributes.

As illustrated in FIGS. 1 and 2, the housing 102 for sterilizing and purifying air is provided as a generally semi-circular configuration to allow it to comfortably attach around a user's neck, torso, waist, etc. The housing 102 defines the body of the device 100, and has a first opening 102-1 and a second opening 102-2. The housing 102 can include at least one partition 202-1 to 202-4 having a plurality of holes (also referred to as "holes", herein), being configured within the housing 102 such that a plurality of compartments 204-1 to 204-3 is formed between the first opening 102-1 and the second opening 102-2. The at least one partition 202-1 to 202-4 can be a flat member having a peripheral shape based on a profile of an internal surface of the housing 102 such that there is no gap between the at least one partition 202-1 to 202-4 and the corresponding inner surface of the housing 102, and the housing 102 allows air to flow only through the holes of the corresponding partitions 202-1 to 202-4. In an exemplary embodiment, the housing 102 can be configured in the form of a flexible first tube 103 having the first opening 102-1 and the second opening 102-2 at two opposite ends of the housing 102. Further, the at least one partition 202-1 to 202-3 can be configured as a perforated disc with holes configured therein. The at least one partition 202-1 to 202-3 can have a diameter equal to an internal diameter of the housing 102 such that there is no gap between the at least one partition 202-1 to 202-4 and the corresponding inner surface of the housing 102, and the housing 102 allows air to flow only through the holes of the corresponding partitions 202-1 to 202-3.

Further, the housing 102 can include at least one ultraviolet (UV) light source 206-1 to 206-3 positioned in each of the plurality of compartments 204-1 to 204-3, which are configured to emit UV light of a predefined wavelength within the plurality of compartments 204-1 to 204-3. The at least one UV light source 206-1 to 206-3 can be a UVC LED light, which is capable of producing ultraviolet at the predefined wavelengths, and high efficiency, with very small amount of power at low voltage levels for a longer period of time. In addition, LEDs used as the UV light sources 206-1 to 206-3 produce no ozone and very little heat.

In an example, when air is expelled through the second opening 102-2 of the housing 102, air inflows into the housing 102 from the first opening 102-1 and flows towards the second opening 102-2 through each of the plurality of compartments 204-1 to 204-3 such that the air flowing through the housing 102 gets sterilized and purified by the emitted UV light from the UV light sources 206-1 to 206-3, and the sterilized and purified air flows out from the second opening 102-2.

In another embodiment, the second opening 102-2 of the housing 102 can be fluidically coupled to a storage tank (not shown) using any or a combination of a mechanical pump, automated pump, and a pipe, which can be configured to supply and store the sterilized and purified air from the housing 102 into the storage tank. The stored air can be later used as required.

The embodiments herein improve conventional air purification systems by providing sterilized and purified breathable air and disinfecting exhaled air. The embodiments herein provide a device 100 comprising a breathing mask 106; a housing 102 operatively connected to the breathing mask 106, wherein the housing 102 comprises a first opening 102-1 and a second opening 102-2, the housing 102 comprising at least one partition 202-1 to 202-3 having a plurality of holes, being configured within the housing 102 such that a plurality of compartments 204-1 to 204-3 is formed between the first opening 102-1 and the second opening 102-2, wherein the housing 102 comprises and is configured as an elongated semi-circular flexible first tube 103 adapted to be worn by the user; and at least one UV light source 206-1 to 206-3 positioned in each of the plurality of compartments 204-1 to 204-3, the at least one UV light source 206-1 to 206-3 configured to emit UV light of a predefined wavelength within the plurality of compartments 204-1 to 204-3, wherein when air is expelled through the second opening 102-2, air inflows into the housing 102 without a fan or pump from the first opening 102-1 and flows towards the second opening 102-2 through each of the plurality of compartments 204-1 to 204-3 such that the air flowing through the housing 102 gets sterilized and purified by the emitted UV light provided by the at least one UV light source 206-1 to 206-3, and the sterilized and purified air flows out from the second opening 102-2.

In an embodiment, the device 100 comprises a breathing mask 106 adapted to be worn over any or a combination of the mouth and nose of the user, and the second opening 102-2 of the housing 102 is fluidically coupled to the breathing mask 106 by a flexible second tube 104 and configured to supply the sterilized and purified air to the user. In an embodiment, the breathing mask 106 comprises an inlet 402 fluidically coupled to the second opening 102-2 of the housing 102, and at least one outlet 404 to facilitate outflow of air being exhaled by the user.

In an embodiment, when air is exhaled by the user into the housing 102, using the breathing mask 106, through the second opening 102-2, the exhaled air flows from the second opening 102-2 towards the first opening 102-1 through each of the plurality of compartments 204-1 to 204-3 such that the exhaled air flowing through the housing 102 gets sterilized and purified by the emitted UV light, and the sterilized and purified air flows out from the first opening 102-1 into atmosphere. In an embodiment, the housing 102 comprises a first one-way valve 208 being configured at the second opening 102-2 to allow outflow of air from the second opening 102-2, and restrict inflow of air into the housing 102 through the second opening 102-2.

In an embodiment, the breathing mask 106 comprises a second one-way valve 406 being configured at each of the at least one outlet 404 to allow outflow of the exhaled air, and restrict inflow of air into the breathing mask 106 through the at least one outlet 404. In an embodiment, any or a combination of an inner surface of the housing 102, and surface of the at least one partition 202-1 to 202-4 are coated with a UVC reflective material. In an embodiment, the housing 102 is in the form of a flexible first tube 103, which is adapted to be accommodated over any or a combination of shoulder, neck, waist, and arms of a user.

In an embodiment, the housing 102 comprises aluminum, and an outer surface of the housing 102 is covered with a plastic cellophane wrap. In an embodiment, one of the at least one partition 202-1 to 202-4 is configured at the first opening 102-1, and the other at least one partition 202-1 to 202-4 are configured at predefined positions along a length of the housing 102 between the first opening 102-1 and the second opening 102-2. In an embodiment, the at least one UV light source 206-1 to 206-3 is a UVC LED light.

In an embodiment, the device 100 comprises an electrical power unit 300 electrically coupled to the at least one UV light source 206-1 to 206-3, and configured to supply electrical power to the at least one UV light source 206-1 to 206-3. In an embodiment, the electrical power unit 300 comprises any or a combination of a charging adapter, batteries, power bank, USB charging port, and electrical power source. In an embodiment, a peripheral shape of the at least one partition 202-1 to 202-3 is based on a profile of an internal surface of the housing 102 such that there is no gap between the at least one partition 202-1 to 202-3 and the corresponding inner surface of the housing 102, and the at least one partition 202-1 to 202-3 allows air to flow only through the corresponding plurality of holes.

In an embodiment, the housing 102 is configured as a flexible first tube 103 having the first opening 102-1 and the second opening 102-2 at two opposite ends of the flexible first tube 103, and the at least one partition 202-1 to 202-4 is configured as a disc. In an embodiment, a diameter of the at least one partition 202-1 to 202-4 is equal to an internal diameter of the flexible first tube 103 such that there is no gap between the inner surface of the flexible first tube 103 and the corresponding at least one partition 202-1 to 202-4, and the at least one partition 202-1 to 202-4 allows air to flow only through the plurality of holes of the corresponding at least one partition 202-1 to 202-4.

According to another example, the embodiments herein provide a housing 102 to facilitate sterilization and purification of air, the housing 102 comprises a first opening 102-1 and a second opening 102-2, at least one partition 202-1 to 202-3 having a plurality of holes being configured within the housing 102 such that a plurality of compartments 204-1 to 204-3 is formed between the first opening 102-1 and the second opening 102-2, wherein the housing 102 is configured as an elongated semi-circular flexible first tube 103 adapted to be worn by a user, and at least one UV light source 206-1 to 206-3 positioned in each of the plurality of compartments 204-1 to 204-3, the at least one UV light source 206-1 to 206-3 configured to emit UV light of a predefined wavelength within the plurality of chambers (i.e. plurality of compartments 204-1 to 204-3), wherein when air is expelled through the second opening 102-2, air inflows into the housing 102, without the need for a fan or pump to push the air, from the first opening 102-1 and flows towards the second opening 102-2 through each of the plurality of compartments 204-1 to 204-3 such that the air flowing through the housing 102 gets sterilized and purified by the emitted UV light, and the sterilized and purified air flows out from the second opening 102-2.

In an embodiment, the housing 102 is shaped and configured as a flexible first tube 103 having the first opening 102-1 and the second opening 102-2 at two opposite ends of the flexible first tube 103, and the at least one partition 202-1 to 202-4 is configured as a disc, and wherein the at least one UV light source 206-1 to 206-3 is a UVC LED light. In an embodiment, the second opening 102-2 of the housing 102 is adapted to be fluidically coupled to any or a combination of a breathing mask 106, and directly to a mouth and nose of a user, using a flexible second tube 104.

In an alternative embodiment, the second opening 102-2 of the housing 102 is fluidically coupled to a breathable storage tank using any or a combination of a mechanical pump, automated pump, and a pipe, which are configured to supply and store the sterilized and purified air from the housing 102 into the storage tank.

In interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A portable air sterilizing device comprising:
    a breathing mask;
    a housing operatively connected to the breathing mask, wherein the housing comprises a first opening and a second opening, wherein the housing comprising at least one partition comprising a first partition having a first plurality of holes, and a second partition having a second plurality of holes, wherein the first partition and the second partition being configured within the housing such that a plurality of compartments is formed by the first partition and the second partition between the first opening and the second opening, and wherein the housing is configured in a shape of an elongated semi-circular flexible first tube adapted to be worn by a user, wherein the housing is adapted to be accommodated over any or a combination of a shoulder, neck, waist, and arms of the user; and
    at least one ultraviolet (UV) light source positioned in each of the plurality of compartments, the at least one UV light source configured to emit UV light of a predefined wavelength within the plurality of compartments,
    wherein air inflows into the housing without a fan or pump through the first opening and flows towards the second opening through each of the plurality of compartments such that the air flowing through the housing gets sterilized and purified by the emitted UV light in each of the plurality of compartments, and the sterilized and purified air flows out from the second opening,
    wherein the air is to flow into a first compartment of the plurality of compartments and is purified by the emitted UV light in the first compartment, wherein the air is then to flow through the first plurality of holes of the first partition and into a second compartment of the plurality of compartments and is purified by the emitted UV light in the second compartment, wherein the air is then to flow through the second plurality of holes of the second partition and into a third compartment of the plurality of compartments and is purified by the emitted UV light in the third compartment,
    wherein any or a combination of an inner surface of the housing, and surface of the at least one partition are coated with a UVC reflective material, and
    wherein the housing comprises aluminum, and an outer surface of the housing is covered with a flexible wrap.

2. The device of claim 1, comprising a third partition configured at the first opening.

3. The device of claim 2, comprising a fourth partition configured at the second opening.

4. The device of claim 3, wherein the third partition comprises a third plurality of holes, and wherein the fourth partition comprises a fourth plurality of holes.

5. The device of claim 4, wherein the air is to flow sequentially through the third plurality of holes of the third partition, then the first plurality of holes of the first partition, then the second plurality of holes of the second partition, and then the fourth plurality of holes of the fourth partition.

6. The device of claim 1, comprising an electrical power unit electrically coupled to the at least one UV light source, and configured to supply electrical power to the at least one UV light source.

7. The device of claim 6, wherein the electrical power unit comprises any of a charging adapter, batteries, power bank, USB charging port, and electrical power source.

8. The device of claim 1, wherein the first opening and the second opening are at two opposite ends of the housing, and the at least one partition is configured in a shape of a disc.

9. The device of claim 8, wherein a diameter of the at least one partition is equal to an internal diameter of the housing such that there is no gap between the inner surface of the housing and a corresponding partition.

10. The device of claim 1, wherein the breathing mask is adapted to be worn over any of a mouth and nose of the user, and wherein the second opening of the housing is fluidically coupled to the breathing mask by a flexible second tube.

11. The device of claim 1, wherein the housing comprises a first one-way valve configured at the second opening to allow outflow of air from the second opening, and restrict inflow of air into the housing through the second opening.

12. The device of claim 1, wherein the at least one UV light source is a UVC LED light.

13. The device of claim 1, wherein a peripheral shape of the at least one partition is based on a profile of an internal surface of the housing such that there is no gap between either the first partition and the second partition and the corresponding inner surface of the housing, and the first partition and the second partition allows air to flow only through the corresponding plurality of holes.

14. The device of claim 1, wherein the air is to flow sequentially through the housing into the first compartment to the second compartment and then to the third compartment in a sequential manner.

15. The device of claim 1, wherein the air is to flow in a semi-circular path through the housing and to follow a semi-circular shape of the housing.

* * * * *